(12) United States Patent
Kreutzian et al.

(10) Patent No.: US 9,506,897 B2
(45) Date of Patent: Nov. 29, 2016

(54) METHODS AND COMPOSITIONS FOR IMPROVED ION-EXCHANGE CHROMATOGRAPHY

(71) Applicant: Agilent Technologies, Inc., Loveland, CO (US)

(72) Inventors: Todd Bruce Kreutzian, Golden, CA (US); Andrew Jackson, Broomfield, CO (US); Paul A. Metz, Lafayette, CO (US); Matthew Waldheim, Loveland, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 253 days.

(21) Appl. No.: 14/025,791

(22) Filed: Sep. 12, 2013

(65) Prior Publication Data

US 2014/0137639 A1 May 22, 2014

Related U.S. Application Data

(60) Provisional application No. 61/727,129, filed on Nov. 16, 2012.

(51) Int. Cl.
*G01N 30/96* (2006.01)

(52) U.S. Cl.
CPC ................... *G01N 30/96* (2013.01)

(58) Field of Classification Search
CPC ............................. G01N 30/96; G01N 30/34
USPC ................. 73/61.55, 61.52; 422/70; 436/161
See application file for complete search history.

(56) References Cited

U.S. PATENT DOCUMENTS

| | | | |
|---|---|---|---|
| 3,905,903 A * | 9/1975 | David ...................... B01J 49/00 210/656 |
| 6,017,457 A | 1/2000 | Gjerde et al. |
| 7,425,263 B2 * | 9/2008 | Tsonev et al. ............. 210/198.2 |
| 7,566,401 B2 | 7/2009 | Kelm et al. |
| 9,193,967 B2 * | 11/2015 | Zhang .............. A61K 47/48215 |
| 2003/0225261 A1 | 12/2003 | Taylor et al. |
| 2005/0011836 A1 * | 1/2005 | Bidlingmeyer ...... B01D 15/166 210/656 |
| 2006/0169638 A1 * | 8/2006 | Zelechonok ......... B01D 15/327 210/635 |
| 2008/0076911 A1 | 3/2008 | Herzer et al. |
| 2009/0239814 A1 | 9/2009 | Manoharan et al. |
| 2009/0286955 A1 * | 11/2009 | Hatala ..................... C07H 21/00 530/344 |
| 2010/0151584 A1 * | 6/2010 | Parsons .............. B01D 15/1864 436/94 |
| 2010/0229634 A1 * | 9/2010 | Yokoyama .................... 73/61.55 |
| 2010/0303893 A1 * | 12/2010 | Luo .......................... C12N 9/78 424/450 |
| 2011/0117660 A1 | 5/2011 | Brooks |
| 2014/0061133 A1 * | 3/2014 | Herman ....................... 210/659 |

FOREIGN PATENT DOCUMENTS

WO 00/12530 A1 3/2000

* cited by examiner

*Primary Examiner* — Laura Martin
*Assistant Examiner* — Suman K Nath

(57) ABSTRACT

The invention generally relates to ion-exchange chromatography. More particularly, the invention relates to compositions and methods that can substantially improve analytical sensitivity and/or selectivity of ion-exchange chromatography as well its efficiency and quality as a purification or preparation tool.

16 Claims, 6 Drawing Sheets

METHODS AND COMPOSITIONS FOR IMPROVED ION-EXCHANGE CHROMATOGRAPHY

PRIORITY CLAIMS AND RELATED PATENT APPLICATIONS

This application claims the benefit of priority from U.S. Provisional Application Ser. No. 61/727,129, filed on Nov. 16, 2012, the entire content of which is incorporated herein by reference in its entirety.

FIELD OF THE INVENTION

The invention generally relates to ion-exchange chromatography. More particularly, the invention relates to compositions and methods that can substantially improve analytical sensitivity and/or selectivity of ion-exchange chromatography as well its efficiency and quality as a purification or preparation tool.

BACKGROUND OF THE INVENTION

Ion-exchange chromatography is a frequently used chromatography technique that separates ions and polar molecules based on their charge. It can be used for almost any type of charged molecule including large proteins, polypeptides, nucleic acids, polynucleotides, small nucleotides and amino acids. The surface of the stationary phase displays ionic functional groups, which interact with analyte ions of opposite charge through columbic (ionic) interactions. Ion-exchange chromatography is thus divided into cation-exchange chromatography and anion-exchange chromatography. In cation-exchange chromatography, positively charged cations are retained because the stationary phase displays a negatively charged functional group, whereas in anion-exchange chromatography, anions are retained by positively charged functional groups on the stationary phase.

Biomolecules are any molecule that are produced by a living organism, including large macromolecules such as nucleic acids, proteins, polysaccharides and lipids, as well as small molecules such as metabolites and natural products. The ability to efficiently and accurately analyze biomolecules is central to the life science, materials and other industries, for example in drug R&D, medical diagnosis, forensic analysis, genetic and food testing. Ion-exchange chromatography is a key technique for analysis and purification, isolation of various types of biomolecules. For example, anion-exchange high-performance liquid chromatography (HPLC) is often an ideal chromatographic mode for oligonucleotide separations. The counter-ionic interaction of the negatively charged analytes and a stationary phase with a surface which displays positively charged functional groups provides for excellent column retention. With optimized analytical parameters, single nucleotide variants (e.g., N−1, N+1) are often chromatographically specified in the presence of longer (~30-40 nt) oligonucleotide sequences.

The separation mode is also applied to oligonucleotides that are conjugated to large (~40K Da) polyethylene-glycol (PEG) moieties. When these molecules are separated under similar analytical conditions, differences in the appearance of the chromatography are noted relative to that observed for the non-PEGylated analogs. Reduced retention times and band broadening in the chromatographic trace are typically found with the PEGylated species. Additionally, impurity peaks are observed with valleys and inflection points presenting with a more 'vague' appearance. Single nucleotide variant selectivity may still be observed with such PEGylated analytes with careful choice of analytical parameters, although the peak resolution of the respective species is often observed to be significantly less. The reduced resolution, sensitivity and recovery could substantially impact analytical and preparative functionalities of ion-exchange chromatography as an effective tool for biomolecules.

Previous attempts at addressing the low recovery of impurities involved adding additional organic solvent (e.g., acetonitrile, isopropanol) to the mobile phase regime and also to perform the analysis at higher temperatures. These measures, however, have been largely ineffective.

Thus, there remains an unmet need for novel approaches that effectively address the issues associated with reduced resolution, sensitivity and recovery and to make ion-exchange HPLC an effective analytical and preparative tool for certain analytes.

SUMMARY OF THE INVENTION

The invention is based in part on the unexpected discovery of a unique approach that successfully address the issues associated with the reduced resolution, sensitivity and recovery in ion-exchange chromatography in handling certain types of analytes. The novel approach entails the inclusion of one or more modifying agents in the mobile phase, and/or pre-treatment of the stationary phase with such modifying agents. Ion-exchange HPLC using such mobile phase or stationary phase displays much improved resolution and sensitivity as well as higher recovery rate.

For instance, the use of the PEG-modified mobile phase regimes when performing anion-exchange HPLC analysis of PEGylated oligonucleotide drug substance resolves the issues of poor analytical sensitivity for low levels of PEGylated impurities. Accurate chromatographic recovery of spiked authentic species is observed with the modification.

In one aspect, the invention generally relates to a method for analyzing or purifying one or more ionic analytes in a sample by anion-exchange chromatography. The method includes: providing an anion-exchange column packed with an anion-exchange stationary phase; providing an anion-exchange mobile phase having a modifying agent; performing anion-exchange chromatography under a condition allowing anion exchange between the one or more ionic analytes in the sample and the anion-exchange stationary phase, thereby separating the one or more ionic analytes in the anion-exchange column; and analyzing and/or collecting the separated one or more ionic analytes.

In another aspect, the invention generally relates to a method for performing anion-exchange chromatography. The method includes adding a modifying agent to a mobile phase prior to performing anion-exchange, wherein the modifying agent is an organic compound comprising at least three units of moiety, wherein the moiety is independently selected from C—O—C moiety or —OH group.

In yet another aspect, the invention generally relates to a method for performing ion-exchange chromatography of a sample comprising an ionic analyte. The method includes adding as an additive a modifying agent to a mobile phase prior to performing ion-exchange chromatography using the mobile phase. In certain embodiments, ion-exchange chromatography is under anion exchange mode. In certain embodiments, the ionic analyte includes a polyethylene glycol-conjugated peptide. In certain embodiments, ion-exchange chromatography is under cation-exchange mode.

In certain embodiments, the ionic analyte includes a polyethylene glycol-conjugated oligonucleotide.

DEFINITIONS

Figure 1:
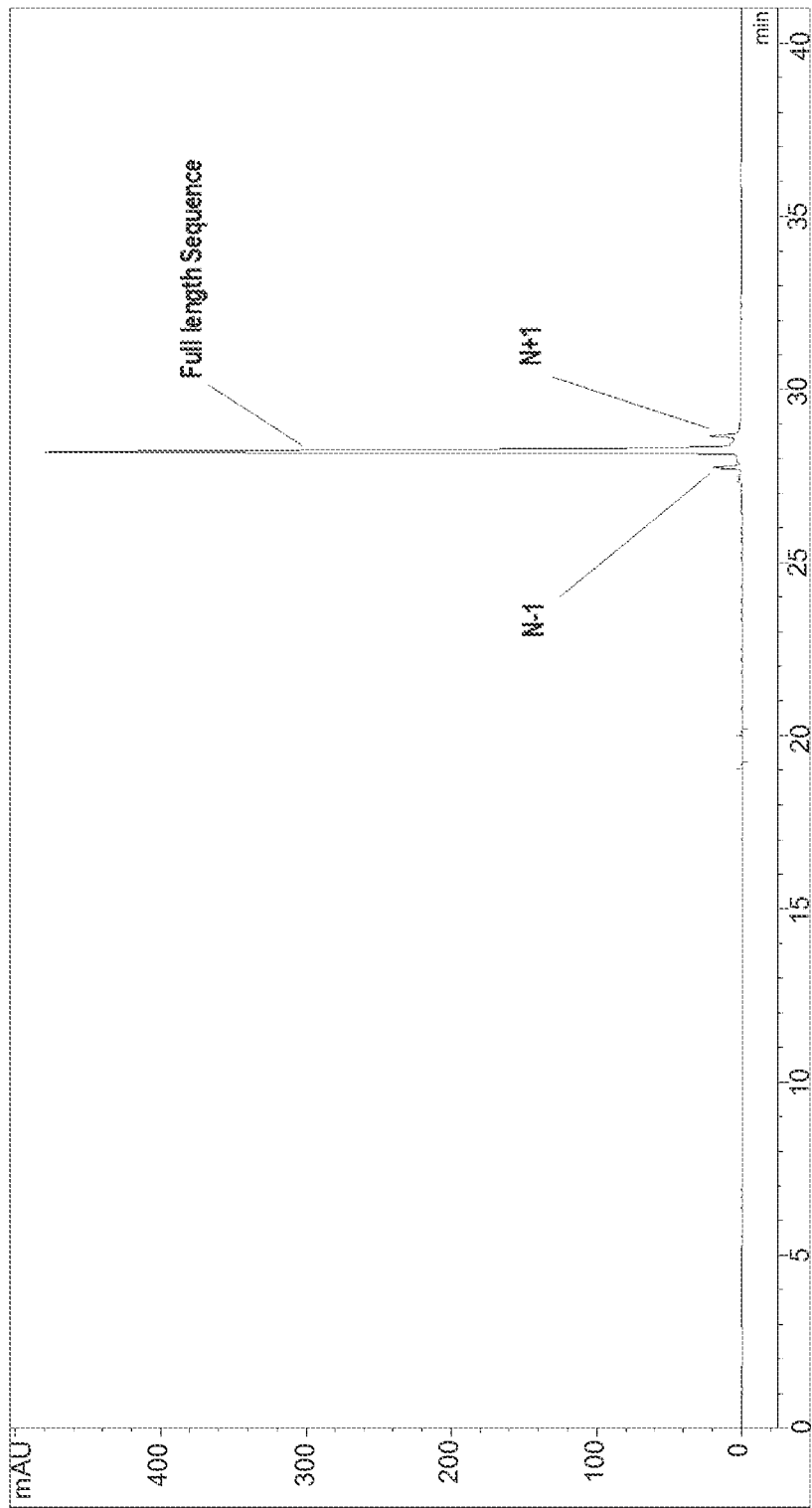
FIG. 1 shows an exemplary anion-exchange HPLC of a representative 30-mer DNA sequence, UV trace at 259 nm.
Figure 1:
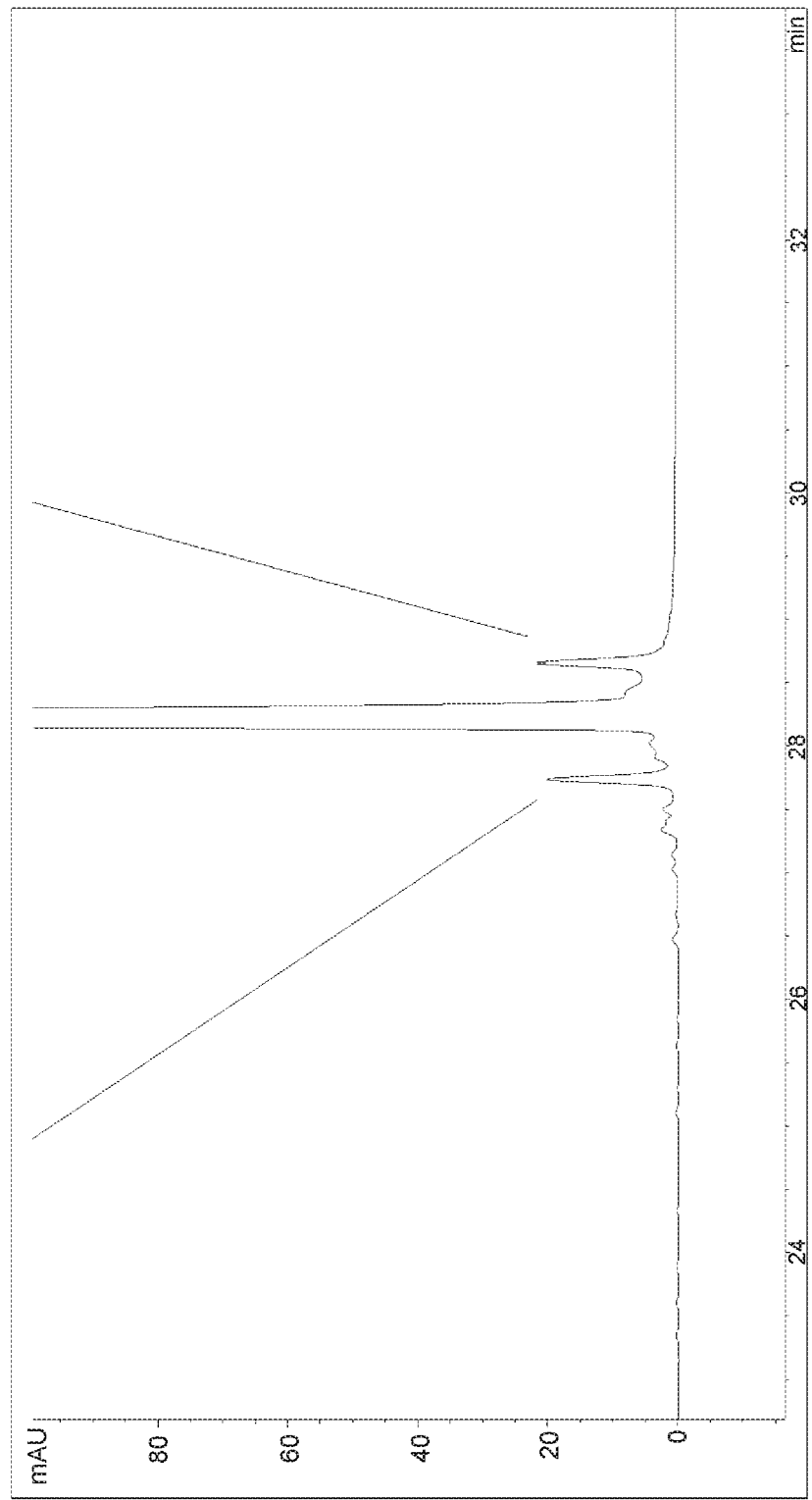

Definitions of chemical terms and functional groups are described in more detail below. General principles of organic chemistry, as well as specific functional moieties and reactivity, are described in "Organic Chemistry", Thomas Sorrell, University Science Books, Sausalito: 1999.

As used herein, the term "alkylene oxide" refers to an organic compound that has a moiety represented by —$R_1$—O—$R_2$—, wherein each of $R_1$ and $R_2$ is a $(CH_2)_n$, wherein n is a positive integer. An oligomeric alkylene oxide (or interchangeably an alkylene oxide oligomer) therefore refers to an oligomeric compound having a number of units of alkylene oxide in linear, branched or block arragements.

As used herein, the term "polyethylene-glycol" (PEG) refers to a polyether compound with having the structure: HO—$CH_2$—($CH_2$—O—$CH_2$—)$_n$—$CH_2$—OH or the moiety —O—$CH_2$—($CH_2$—O—$CH_2$—)$_n$—$CH_2$—O—, where n is a positive integer typically in the range of from about 3 to about 500 (e.g., from about 3 to about 200, from about 3 to about 100 from about 5 to about 500, from about 10 to about 500, from about 50 to about 500).

As used herein, the term "analytes" refers to a component, a substance or chemical constituent that is of present in a sample subject to analysis, measurement or purification. Analyte, therefore, not only refers to components of analytical interest but also components that are to be purified, isolated or collected.

As used herein, the term "antibody" refers to molecules that are capable of binding an epitope or antigenic determinant. The term is meant to include whole antibodies and antigen-binding fragments thereof, including single-chain antibodies. The antibodies can be from any animal origin. Preferably, the antibodies are mammalian, e.g., human, murine, rabbit, goat, guinea pig, camel, horse and the like, or other suitable animals. Antibodies may recognize polypeptide or polynucleotide antigens. The term includes active fragments, including for example, an antigen binding fragment of an immunoglobulin, a variable and/or constant region of a heavy chain, a variable and/or constant region of a light chain, a complementarity determining region (cdr), and a framework region. The terms include polyclonal and monoclonal antibody preparations, as well as preparations including hybrid antibodies, altered antibodies, chimeric antibodies, hybrid antibody molecules, $F(ab)_2$ and F(ab) fragments; Fv molecules (for example, noncovalent heterodimers), dimeric and trimeric antibody fragment constructs; minibodies, humanized antibody molecules, and any functional fragments obtained from such molecules, wherein such fragments retain specific binding. The use of the singular terms "a" or "an" or "the" antibody are not meant to be limited to a single antibody when it is clear that more than one antibody is present in the composition or preparation. In addition, unless indicated otherwise, the singular term for "antibody" may include a collection of antibodies that are not necessarily heterogenous in their structures or specificities.

As used herein, the term "C—O—C moiety" refers to an organic compound that has a carbon-oxygen-carbon bond.

As used herein, the term "nucleic acid," "nucleotide," "oligonucleotide," "polynucleotide," and "nucleic acid molecule" are used interchangeably herein to refer to polymeric forms of nucleotides (ribonucleotides or deoxyribonucleotides, or analogs thereof) of any length. They can include both double- and single-stranded sequences and include, but are not limited to, cDNA from viral, prokaryotic, and eukaryotic sources; mRNA; genomic DNA sequences from viral (e.g., DNA viruses and retroviruses) or prokaryotic sources; RNAi; cRNA; antisense molecules; ribozymes; and synthetic DNA sequences. The term also captures sequences that include any of the known base analogs of DNA and RNA.

As used herein, the term "oligomeric" refers to the characteristic of an organic compound that has at least one structural repetitive unit.

As used herein, the term "polyol" refers to an organic compound with three or more hydroxyl (—OH) functional groups.

As used herein, the terms "protein," "peptide" or "polypeptide" are used interchangeably to refer to a polymer of amino acid residues, and are not limited to a minimum length. Thus, peptides, oligopeptides, dimers, multimers, and the like, are included within the definition. Both full-length proteins and fragments thereof are encompassed by the definition. The terms also include post-expression modifications of the polypeptide, for example, glycosylation, acetylation, phosphorylation, and the like. Furthermore, a "polypeptide" may refer to a protein which includes modifications, such as deletions, additions, and substitutions (generally conservative in nature), to the native sequence, as long as the protein maintains the desired activity. These modifications may be deliberate or may be accidental.

DETAILED DESCRIPTION OF THE INVENTION

This invention provides novel approach that successfully address the issues associated with the reduced resolution, sensitivity and recovery in ion-exchange chromatography in handling certain types of analytes. The much improved and versatile approach entails the inclusion of one or more modifying agent in the mobile phase, and/or pre-treatment of the stationary phase with such modifying agents. Ion-exchange HPLC using such mobile phase or stationary phase displays much improved resolution and sensitivity as well as higher recovery rate. In certain preferred embodiments, for example, the use of the PEG-modified mobile phase regimes when performing anion-exchange HPLC analysis of PEGylated oligonucleotide drug substance substantially increases analytical sensitivity for low levels of PEGylated impurities.

Anion-exchange HPLC is an often-used chromatographic mode for separation of oligonucleotides. When analytical parameters are optimized, single nucleotide variants (e.g., N−1, N+1) are often chromatographically specified in the presence of longer (~30-40 nt) oligonucleotide sequences. For example, as shown in FIG. 1 with the single nucleotide variants labeled, the UV detector trace (at 259 nm) displays a clean oligonucleotide separation.

Figure 2:
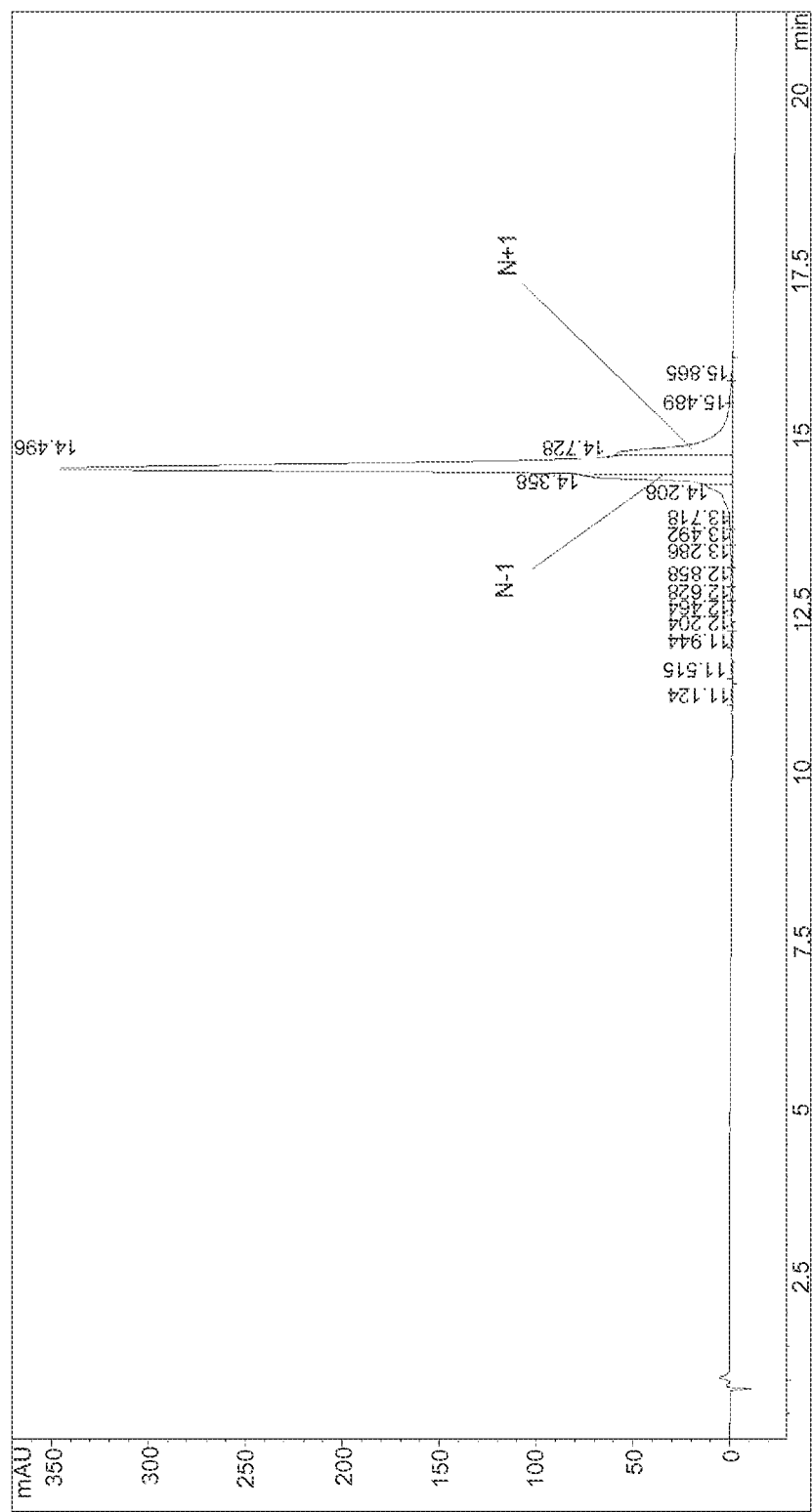
FIG. 2 shows an exemplary anion-exchange HPLC of a representative 40-mer PEGylated oligonucleotide sequence, UV trace at 259 nm.
Figure 2:
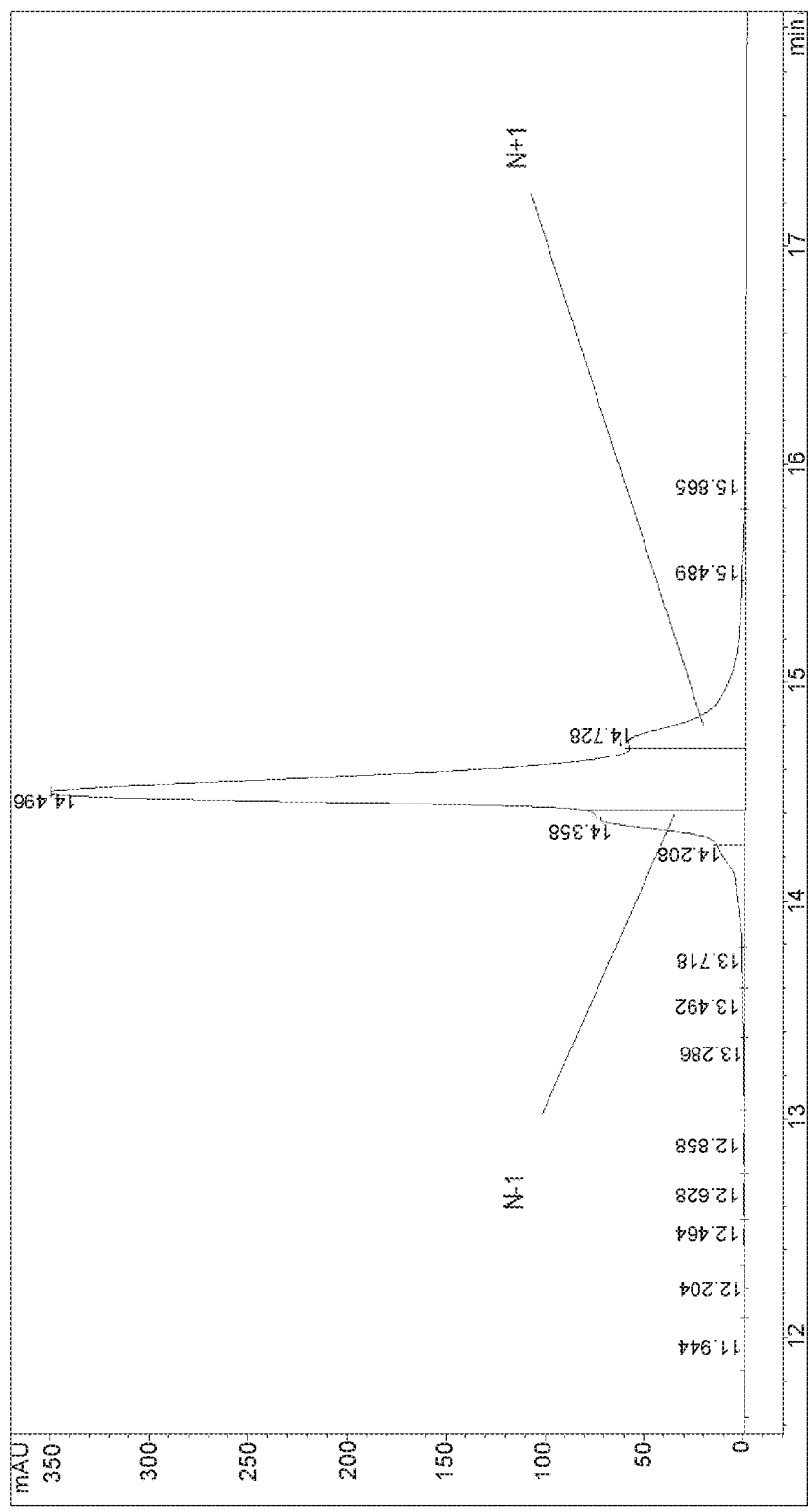

When separating PEGylated oligonucleotides under similar analytical conditions, differences in the appearance of the chromatography are noted relative to that observed for the non-PEGylated analogs. Higher values relative to non-PEGylated analogs for lower limits of detection (LOD) and quantitation (LOQ) are often observed for PEGylated oligonucleotides. Reduced retention times and band broadening in the chromatographic trace are typically found. Impurity peaks are observed with valleys and inflection points presenting with a more 'vague' appearance. Peak resolution of the respective species is often much lower. The typical linear correlation of sample load on the column and UV detector response becomes quite poor when observing PEGylated oligonucleotide analytes present at levels below about 1% (w/w) of the nominal sample concentration. This non-linearity is due to poor analyte recovery at low on-column sample loads. The UV detector trace of a typical PEGylated oligonucleotide separation is shown below in FIG. 2, with the single nucleotide variants labeled. When a series of standards are prepared consisting of the PEGylated oligonucleotide at the method-defined concentration spiked with varying levels of an authentic length-based PEGylated impurity, the injections indicate poor chromatographic recovery of the spiked species.

Unity extinction at the wavelength of detection was reasonably assumed for each species on a w/w basis. The peak signal-to-noise (S/N) values for the spiked impurity were calculated as the quotient of peak height and baseline noise (peak-to-peak noise in a baseline region free from injection interference), and the chromatographic recovery was calculated as the ratio of the impurity peak area % (of total detector response due to sample load) and the theoretical w/w % of the spiked material (as-is weight basis).

Because good chromatographic recoveries were consistently observed for samples with non-PEGylated impurities spiked into non-PEGylated oligonucleotide sample solutions, it was assumed that the observed poor recovery with PEGtlated oligonucleotide sample solutions was due to the presence of the PEG moiety associated with the analytes. Without wishing to be bound, an interpretation of the observed poor recovery is based on the presence of the PEG moiety associated with the analytes. In addition to interfering with the counter-ionic interactions of the column phase and the negatively charged oligonucleotide backbone, the PEG may also interact with the surface of the hydrophobic polymeric phase support of the non-porous beads. If the analytes display affinity, a portion of the sample load will adsorb on these surfaces and fail to fully partition along the chemical phase. The dispersed adsorbed analyte may then just 'bleed' off the column and never appear as a peak in the detector trace, effectively compromising the observed chromatographic recovery. It was considered that the adsorption of the analyte on the column support beads may be limited, and that saturating the sites with a suitable proxy might allow the sample load to proceed unheeded across the column chemistry.

In one aspect, the invention generally relates to a method for analyzing or purifying one or more ionic analytes in a sample by anion-exchange chromatography. The method includes: providing an anion-exchange column packed with an anion-exchange stationary phase; providing an anion-exchange mobile phase having a modifying agent; performing anion-exchange chromatography under a condition allowing anion exchange between the one or more ionic analytes in the sample and the anion-exchange stationary phase, thereby separating the one or more ionic analytes in the anion-exchange column; and analyzing and/or collecting the separated one or more ionic analytes.

The condition under which the anion-exchange chromatography is performed is dependent on the applicant at hand, the nature and amount of the analyte(s) and the modifying agents employed, as well as whether it is analytical or preparative chromatography. Guided by the present disclosure, one of ordinary skill in the art will be able to identify the condition(s) under which to perform the chromatography.

The analytes may be any components (including impurities), for example, nucleic acids (e.g., oligonucleotides, oligonucleosides, aptamers), peptides (e.g., proteins, polypeptides, antibodies, antibody fragments), polysaccharides (e.g., arabinoxylans, celluloses, chitins, pectins), lipids (e.g., fats, sterols, monoglycerides, diglycerides, triglycerides, phospholipids), metabolites (e.g., primary metabolites, secondary metabolites), and natural products (e.g., extracted from terrestrial plants, marine organisms, microorganism fermentation broths). These analytes may or may not be conjugated with one or more moieties, such as polyol, polyethylene-glycol (i.e., PEGylated), etc.

Compounds and components that may be found in samples suitable for analysis by the methods disclosed herein include, for example, compounds that are conjugated with one or more of poly(urethanes), poly(siloxanes), poly (methyl methacrylate), poly(vinyl alcohol), poly(ethylene), poly(vinyl pyrrolidone). Non-limiting examples include poly(2-hydroxy ethyl methacrylate), poly(N-vinyl pyrrolidone), poly(methyl methacrylate), poly(vinyl alcohol), poly (acrylic acid), polyacrylamide, poly(ethylene-co-vinyl acetate), poly(ethylene glycol), poly(methacrylic acid), polylactides, polyglycolides, poly-L-glutamic acid, poly (lactide-co-glycolides), polyanhydrides, polyorthoesters.

In certain embodiments, at least one of the one or more ionic analytes includes a compound comprising a polyethylene-glycol moiety. In certain embodiments, at least one of the one or more ionic analytes comprises a polyethylene glycol-conjugated oligonucleotide/polypeptide. In certain embodiments, the polyethylene glycol-conjugated oligonucleotide/polypeptide includes from about 3 k Da to about 100 k Da of polyethylene oxide (e.g., from about 3 k Da to about 100 k Da, from about 3 k Da to about 75 k Da, from about 3 k Da to about 50 k Da, from about 3 k Da to about 30 k Da, from about 3 k Da to about 20 k Da, from about 3 k Da to about 10 k Da, from about 5 k Da to about 100 k Da, from about 10 k Da to about 100 k Da, from about 10 k Da to about 100 k Da, from about 30 k Da to about 100 k Da, from about 50 k Da to about 100 k Da). In certain embodiments, the polyethylene glycol-conjugated oligonucleotide includes from about 5 to about 2,000 units of nucleotides (e.g., from about 5 to about 2,000 units, from about 5 to about 1,500 units, from about 5 to about 1,000 units, from about 5 to about 500 units, from about 5 to about 200 units, from about 5 to about 100 units, from about 5 to about 50 units, from about 10 to about 2,000 units, from about 50 to about 2,000 units, from about 100 to about 2,000 units, from about 500 to about 2,000 units, from about 1,000 to about 2,000 units, from about 1,500 to about 2,000 units).

An analyte may be present at any suitable concentration, for example, at a concentration from about 0.05 μM to about 500 μM (e.g., from about 0.05 μM to about 400 μM, from about 0.05 μM to about 300 μM, from about 0.05 μM to about 200 µM, from about 0.05 µM to about 100 µM, from about 0.05 µM to about 50 µM, from about 0.05 µM to about 30 µM, from about 0.05 µM to about 20 µM, from about 0.05 µM to about 10 µM, from about 0.05 µM to about 5 µM, from about 0.05 µM to about 3 µM, from about 0.05 µM to about 2 µM, from about 0.05 µM to about 1 µM, from about 0.05 µM to about 0.5 µM, from about 0.1 µM to about 500 µM, from about 0.5 µM to about 500 µM, from about 1 µM to about 500 µM, from about $2_1$LIM to about 500 µM, from about 5 µM to about 500 µM, from about 10 µM to about 500 µM, from about 20 µM to about 500 µM, from about 30 µM to about 500 µM, from about 50 µM to about 500 µM, from about 100 µM to about 500 µM).

Depending on the analytes, modifying agents suitable for use in the disclosed methods may be selected, for example, among poly(urethanes), poly(siloxanes), poly(methyl methacrylate), poly(vinyl alcohol), poly(ethylene), poly(vinyl pyrrolidone). Non-limiting examples include poly(2-hydroxy ethyl methacrylate), poly(N-vinyl pyrrolidone), poly (methyl methacrylate), poly(vinyl alcohol), poly(acrylic acid)., polyacrylamide, poly(ethylene-co-vinyl acetate), poly(ethylene glycol), poly(methacrylic acid), polylactides, polyglycolides, poly-L-glutamic acid, poly(lactide-co-glycolides), polyanhydrides, polyorthoesters.

In certain embodiments, the modifying agent is an organic compound having at least three units of moiety wherein the moiety is independently selected from C—O—C moiety or —OH group.

In certain embodiments, the modifying agent includes a polyol moiety. In certain embodiments, the modifying agent includes an oligomeric alkylene oxide moiety. In certain embodiments, the modifying agent is an alkylene oxide oligomer. In certain embodiments, the alkylene oxide oligomer is an ethylene oxide oligomer. The ethylene oxide oligomer may include any suitable molecular weight, for example, from about 3 k Da to about 100 k Da (e.g., from about 3 k Da to about 100 k Da, from about 3 k Da to about 75 k Da, from about 3 k Da to about 50 k Da, from about 3 k Da to about 30 k Da, from about 3 k Da to about 20 k Da, from about 3 k Da to about 10 k Da, from about 5 k Da to about 100 k Da, from about 10 k Da to about 100 k Da, from about 10 k Da to about 100 k Da, from about 30 k Da to about 100 k Da, from about 50 k Da to about 100 k Da).

The modifying agent may be present in the anion-exchange mobile phase at any suitable concentration, for example, from about 0.1 µM to about 100 µM (e.g., from about 0.1 µM to about 50 µM, from about 0.1 µM to about 30 µM, from about 0.1 µM to about 20 µM, from about 0.1 µM to about 10 µM, from about 0.1 µM to about 5 µM, from about 0.1 µM to about 3 µM, from about 0.1 µM to about 2 µM, from about 0.1 µM to about 1 µM, from about 0.5 µM to about 100 µM, 1 µM to about 100 µM, 2 µM to about 100 µM, 5 µM to about 100 µM, 10 µM to about 100 µM, 20 µM to about 100 µM, 30 µM to about 100 µM, 50 µM to about 100 µM).

The sensitivity of anion-exchange chromatography using the anion-exchange mobile phase with the modifying agent is greater than, for example at least 2 fold greater than, that of anion-exchange chromatography using the same anion-exchange mobile phase without the modifying agent. In certain embodiments, the sensitivity of anion-exchange chromatography using the anion-exchange mobile phase with the modifying agent is at least 3 fold greater than, preferably at least 5 fold greater than, that of anion-exchange chromatography using the same anion-exchange mobile phase without the modifying agent. In certain embodiments, the sensitivity of anion-exchange chromatography using the anion-exchange mobile phase with the modifying agent is at least 10 fold greater than that of anion-exchange chromatography using the same anion-exchange mobile phase without the modifying agent.

In another aspect, the invention generally relates to a method for performing anion-exchange chromatography. The method includes adding a modifying agent to a mobile phase prior to performing anion-exchange, wherein the modifying agent is an organic compound comprising at least three units of moiety, wherein the moiety is independently selected from C—O—C moiety or —OH group.

In yet another aspect, the invention generally relates to a method for performing ion-exchange chromatography of a sample comprising an ionic analyte. The method includes adding as an additive a modifying agent to a mobile phase prior to performing ion-exchange chromatography using the mobile phase.

In certain embodiments, the ion-exchange chromatography is performed under anion-exchange mode. In certain embodiments, the ionic analyte includes a polyethylene glycol-conjugated polypeptide or oligonucleotide.

In certain embodiments, the ion-exchange chromatography is performed under cation-exchange mode. In certain embodiments, the ionic analyte includes a polyethylene glycol-conjugated oligonucleotide or polypeptide.

Unity extinction at the wavelength of detection was reasonably assumed for each species on a w/w basis. The peak signal-to-noise (S/N) values for the spiked impurity were calculated as the quotient of peak height and baseline noise (peak-to-peak noise in a baseline region free from injection interference), and the chromatographic recovery was calculated as the ratio of the impurity peak area % (of total detector response due to sample load) and the theoretical w/w % of the spiked material (as-is weight basis).

The use of non-functionalized Polyethylene Glycol with average molar mass of 40K Da was evaluated as a mobile phase additive/modifier. When the PEG was incorporated into the mobile phase at levels of 0.10-0.15 mg/mL (2.5-3.9 µM), the detection of low levels of PEGylated oligonucleotide Drug substance impurities was enabled and >90% chromatographic recovery was observed in those samples spiked with known amounts of authentic impurities. The experimental results were corroborated over three different anion exchange HPLC analysis methods applicable to three different PEGylated oligonucleotide Drug Substances. The evaluations were limited to those analytical columns using pellicular anion exchange resin consisting of quaternary amine functionality and a nonporous polymeric substrate, specifically the Dionex DNAPac PA100 and PA200 models.

Figure 3:
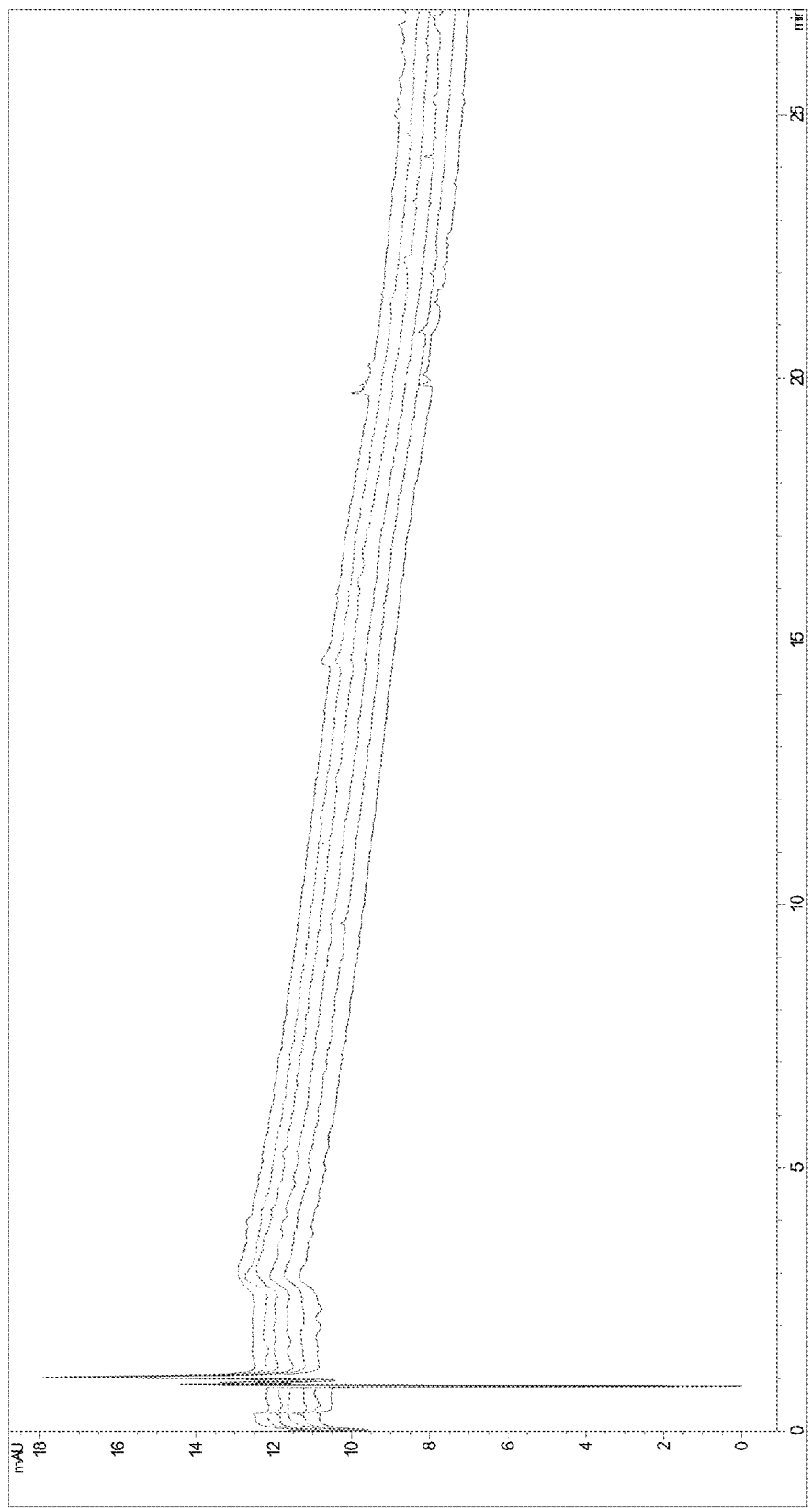
FIG. 3 shows an exemplary anion-exchange HPLC of dilute solutions of PEGylated oligonucleotide drug substance by original analysis conditions. The stacked plots (UV trace at 258 nm) represent six overlaid chromatograms of solutions ranging from 0.04 µM to 0.2 µM drug substance. A signal (at 14.5 min.) is observed for only the most concentrated of the solutions.
Figure 4:
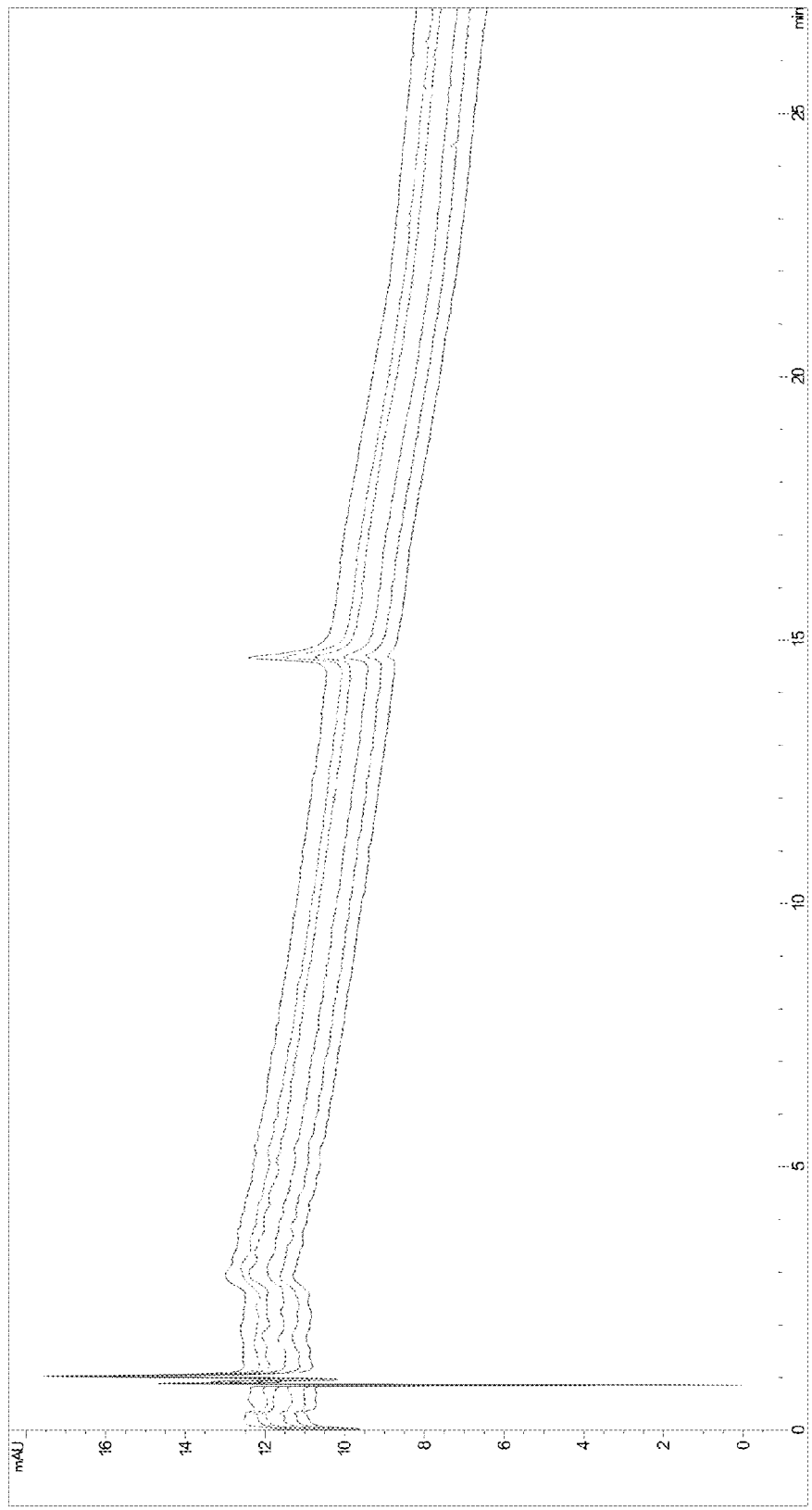
FIG. 4 shows an exemplary anion-exchange HPLC of solutions with utilization of a mobile phase modifying agent.

FIG. 3 shows exemplary anion-exchange HPLC of very dilute solutions of PEGylated oligonucleotide drug substance by original analysis conditions. The stacked plots (UV trace at 258 nm) represent six overlaid chromatograms of solutions ranging from 0.04 µM to 0.2 µM Drug Substance. A signal (at 14.5 min) was observed for only the most concentrated of the solutions. FIG. 4 shows exemplary anion-exchange HPLC of the same solutions under identical analysis conditions but with utilization of the mobile phase modifying agent.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples disclosed herein are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain important additional information, exemplification and guidance that can be adapted to the practice of this invention in its various embodiments and equivalents thereof.

The invention claimed is:

1. A method for analyzing or purifying one or more ionic analytes in a sample by anion-exchange chromatography, comprising:
providing an anion-exchange column packed with an anion-exchange stationary phase;
providing an anion-exchange mobile phase having a modifying agent;
performing anion-exchange chromatography under a condition allowing anion exchange between the one or more ionic analytes in the sample and the anion-exchange stationary phase, thereby separating the one or more ionic analytes in the anion-exchange column; and
analyzing and/or collecting the separated one or more ionic analytes;
wherein:
the modifying agent is an alkylene oxide oligomer comprising at least three units of an alkylene oxide moiety; and
at least one of the one or more ionic analytes comprises a polyethylene-glycol moiety.

2. The method of claim 1, wherein at least one of the one or more ionic analytes comprises a polyethylene glycol-conjugated oligonucleotide.

3. The method of claim 2, wherein the polyethylene glycol-conjugated oligonucleotide comprises from about 3 k Da to about 100 k Da of polyethylene oxide and from about 5 to about 2,000 units of nucleotides.

4. The method of claim 1, wherein the modifying agent is an ethylene oxide oligomer.

5. The method of claim 4, wherein the ethylene oxide oligomer comprises from about 3 k Da to about 100 k Da of polyethylene oxide.

6. The method of claim 1, wherein the modifying agent is present in the anion-exchange mobile phase at a concentration from about 0.1 µM to about 100 µM.

7. The method of claim 1, wherein each of the one or more analytes is present in the sample at a concentration from about 0.05 µM to about 500 µM, wherein the concentration is based on the non-conjugated moiety of the analytes.

8. The method of claim 1, wherein the sensitivity of anion-exchange chromatography using the anion-exchange mobile phase with the modifying agent is at least 2 fold greater than that of anion-exchange chromatography using the same anion-exchange mobile phase without the modifying agent.

9. A method for performing anion-exchange chromatography comprising adding a modifying agent to a mobile phase prior to performing anion-exchange, wherein the modifying agent is an alkylene oxide oligomer comprising at least three units of an alkylene oxide moiety.

10. The method of claim 9, wherein the modifying agent is an ethylene oxide oligomer.

11. The method of claim 9, wherein the modifying agent is present in the anion-exchange mobile phase at a concentration from about 0.1 µM to about 100 µM.

12. A method for performing ion-exchange chromatography of a sample comprising an ionic analyte, the method comprising adding as an additive a modifying agent to a mobile phase prior to performing ion-exchange chromatography using the mobile phase, wherein the modifying agent is an alkylene oxide oligomer comprising at least three units of an alkylene oxide moiety and the ionic analyte comprises a polyethylene-glycol moiety.

13. The method of claim 12, wherein the ion-exchange chromatography is anion exchange chromatography.

14. The method of claim 12, wherein the ionic analyte is a polyethylene glycol-conjugated oligonucleotide or polypeptide.

15. The method of claim 12, wherein the alkylene oxide oligomer is an ethylene oxide oligomer.

16. The method of claim 15, wherein the ethylene oxide oligomer comprises from about 3 k Da to about 100 k Da of polyethylene oxide.

* * * * *

UNITED STATES PATENT AND TRADEMARK OFFICE
CERTIFICATE OF CORRECTION

| | | |
|---|---|---|
| PATENT NO. | : 9,506,897 B2 | Page 1 of 1 |
| APPLICATION NO. | : 14/025791 | |
| DATED | : November 29, 2016 | |
| INVENTOR(S) | : Todd Bruce Kreutzian et al. | |

It is certified that error appears in the above-identified patent and that said Letters Patent is hereby corrected as shown below:

In the Claims

In Column 3, Line 34, delete "arragements." and insert -- arrangements. --, therefor.

In Column 4, Line 9, delete "heterogenous" and insert -- heterogeneous --, therefor.

In Column 5, Line 43, delete "PEGtlated" and insert -- PEGylated --, therefor.

In Column 7, Line 9, delete "$2_1$LIM" and insert -- 2 µM --, therefor.

Signed and Sealed this
Seventh Day of February, 2017

Michelle K. Lee
*Director of the United States Patent and Trademark Office*